US009867977B2

(12) United States Patent
Sumners et al.

(10) Patent No.: US 9,867,977 B2
(45) Date of Patent: Jan. 16, 2018

(54) APPARATUS AND METHOD FOR PROVIDING ELECTRICAL STIMULATION TO A SUBJECT

(75) Inventors: David Paul Sumners, Walton on Thames (GB); Katya Nikolova Mileva, London (GB)

(73) Assignee: Actegy Limited (GB)

( * ) Notice: Subject to any disclaimer, the term of this patent is extended or adjusted under 35 U.S.C. 154(b) by 29 days.

(21) Appl. No.: 13/825,113

(22) PCT Filed: Aug. 13, 2012

(86) PCT No.: PCT/GB2012/000657
§ 371 (c)(1),
(2), (4) Date: May 14, 2013

(87) PCT Pub. No.: WO2013/024241
PCT Pub. Date: Feb. 21, 2013

(65) Prior Publication Data
US 2013/0331907 A1    Dec. 12, 2013

(30) Foreign Application Priority Data
Aug. 12, 2011    (GB) .................................. 1113937.5

(51) Int. Cl.
*A61N 1/04*  (2006.01)
*A61N 1/36*  (2006.01)
(Continued)

(52) U.S. Cl.
CPC ....... *A61N 1/0472* (2013.01); *A61N 1/36003* (2013.01); *A63B 22/16* (2013.01);
(Continued)

(58) Field of Classification Search
CPC .............. A61N 1/0472; A61N 1/36003; A61N 1/0452; A61N 1/322; A61N 1/36014
See application file for complete search history.

(56) References Cited

U.S. PATENT DOCUMENTS 2,553,873 A    5/1951    Schwebel, Sr.
5,358,513 A    10/1994   Powell et al.
(Continued)

FOREIGN PATENT DOCUMENTS

CN    1408325 A    9/2001
CN    1408325 A    4/2003
(Continued)

OTHER PUBLICATIONS

Electronic Filing Receipt for request for grant of patent, application No. GB1113937.5 dated Aug. 12, 2011, 27 pages.
(Continued)

*Primary Examiner* — Michael Kahelin
(74) *Attorney, Agent, or Firm* — Arnold & Saunders, LLP; Christopher McKeon

(57) ABSTRACT

An apparatus for the electrical stimulation of a subject is provided, the apparatus comprising a contact member having a contact surface for contacting the plantar surface of a foot of the subject; and means for providing an electrical stimulation cycle to the foot of the subject comprising supplying an electrical current to the contact surface for the electrical stimulation of the plantar muscles of the foot of the subject; wherein the contact surface is moveable so as to allow the angle of the joints of the foot and ankle of the subject to change during the electrical stimulation cycle.

10 Claims, 6 Drawing Sheets

(51) Int. Cl.
*A63B 22/16* (2006.01)
*A61N 1/32* (2006.01)

(52) U.S. Cl.
CPC ............ *A61N 1/0452* (2013.01); *A61N 1/322* (2013.01); *A61N 1/36014* (2013.01); *A63B 2213/004* (2013.01)

(56) References Cited

U.S. PATENT DOCUMENTS

| | | | |
|---|---|---|---|
| 6,569,213 B1 * | 5/2003 | Busch | 48/79 |
| 6,615,080 B1 | 9/2003 | Unsworth et al. | |
| D496,468 S | 9/2004 | Park | |
| 2006/0085047 A1 | 4/2006 | Unsworth et al. | |
| 2006/0174522 A1 * | 8/2006 | Yu | A43B 3/00 36/141 |

FOREIGN PATENT DOCUMENTS

| | | | |
|---|---|---|---|
| CN | 200973920 Y | 11/2007 | |
| CN | 102058200 A | 12/2010 | |
| CN | 102058200 A | 5/2011 | |
| DE | 20303923 U1 | 12/2003 | |
| GB | 2493904 B | 3/2014 | |
| JP | 2001000496 A | 1/2001 | |
| WO | 03030805 A1 | 4/2003 | |
| WO | 2004080528 A2 | 9/2004 | |
| WO | 2008005865 A1 | 1/2008 | |

OTHER PUBLICATIONS

Patents Act 1977: Patents Rules 2007 Report Under Section 15A, based on application No. GB1113937.5, dated Aug. 18, 2011, 2 pages.
Electronic Filing Receipt for statement of inventorship form 7 dated Aug. 13, 2012, 1 page.
Patents Act 1977: Patents Rules 2007 Notice of publication, based on application No. GB1113937.5, dated Jan. 28, 2013, 25 pages.
Response to combined search and examination report dated Nov. 21, 2011 based on application No. GB1113937.5, filed Oct. 14, 2013, 3 pages.
Patents Act 1977: Examination Report Under Section 18(3) based on application No. GB1113937.5, Nov. 26, 2013, 2 pages.
Response to examination report dated Nov. 26, 2013, filed Dec. 27, 2013, based on application No. GB1113937.5, 30 pages.
Patents Act 1977: Patents Rules 2007 Notification of Grant: Patent Serial No. GB2493904, dated Feb. 18, 2014, 25 pages.
Related GB divisional application No. GB1320123.1 prosecution history through Feb. 10, 2014, including UK IPO Office Actions dated Nov. 26, 2013 and Feb. 10, 2014.
International Search Report based on International application No. PCT/GB2012/000657, Form PCT/ISA/210, dated Oct. 19, 2012, 5 pages.
Search Report Under Section 17 based on application No. GB1113937.5, dated Nov. 16, 2011, 1 page.
High Tech Health "Circulation Booster" [online] available from: http:www.circulationboosterco.uk/products/Circulation-Booster-v3/[Accessed Nov. 15, 2011], 1 page.
Combined Search and Examination Report Under Sections 17 and 18(3) based on application No. GB1113937.5, dated Nov. 21, 2011, 3 pages.
Combined Search and Examination Report Under Sections 17 and 18(3) based on application No. GB11320123.1, dated Nov. 26, 2013, 3 pages.
International Preliminary Report on Patentability and Written Opinion of the International Searching Authority based on International application No. PCT/GB2012/000657, form PCT/IB/373, dated Feb. 18, 2014, 8 pages.
Response made to Report under Section 18(3) for application No. GB11320123.1, dated Feb. 10, 2014, 1 page, issued by Intellectual Property Office.
http://futuresz.manufacturer.globalsources.com/si/6008829771990/pdtl/Electric-foot/1059199849/Foot-massager.htm#ProductCertification, [Accessed Nov. 25, 2013].

* cited by examiner

APPARATUS AND METHOD FOR PROVIDING ELECTRICAL STIMULATION TO A SUBJECT

The present invention relates to a method for providing electrical stimulation to a subject, in particular to the feet of a subject. The present invention further relates to an apparatus for performing the same.

The electrical stimulation of a subject for improving circulation is known in the art. In particular, the electrical stimulation of the feet and legs of a subject to improve venous bloodflow is known and reported in the art. Thus, Kaplan, R. E. et al., 'Electrical foot stimulation and implications for the prevention of venous thromboembolic disease', (Thrombosis and haemostasis, 2002, vol. 88, no 2, pages 200 to 204) describe the results of experiments conducted on subjects, in which mild electrical stimulation was applied to the calf or plantar muscles of the subject. Analysis showed an increase in the venous femoral and popliteal blood flow of the side of the subject to which electrical stimulation was applied, compared with the non-stimulated side.

Further, W Man, I. O., et al. 'Effect of neuromuscular electrical stimulation on foot/ankle volume during standing' (Med Sci Sports Exerc., 2003, April, 35(4), pages 630 to 634) report that the neuromuscular electrical stimulation of the lower leg muscles of a subject prevented the increase in volume of the feet and ankles generally experienced after extended periods of standing. It was concluded that neuromuscular electrical stimulation provided a means for reducing swelling in the lower limbs of subjects that are not capable of fully activating their musculo-venous pumps.

Faghri, P. D., et al., 'Electrical stimulation-induced contraction to reduce blood stasis during arthroplasty' (IEEE Trans Rehabil Eng., 1997, March, 5(1), pages 62 to 69) report data suggesting that continuous electrical stimulation-induced contractions could improve lower leg circulation in subjects by eliciting the physiologic muscle pump. This will lead, in turn, to improved venous circulation and a reduction of blood stasis, for example during total hip and/or knee surgery. The authors suggest this technique may offer greater protection against deep vein thrombosis (DVT) and pulmonary embolism (PE) during surgery than the commonly used sequential compression devices and techniques.

Faghri, P. D., et al., 'Venous hemodynamics of the lower extremities in response to electrical stimulation' (Arch Phys Med Rehabil., 1998, July, 79(7), pages 842 to 848) concluded from experiments conducted that periodic single electrostimulation-induced calf muscle contractions produced significant muscle pump function and could be used to improve venous blood flow and reduce stasis in the lower leg, while continuous electrostimulation-induced contractions could improve lower leg peripheral perfusion while eliciting the physiologic venous muscle pump.

Anderson, S. I., et al., 'Chronic transcutaneous electrical stimulation of calf muscles improves functional capacity without inducing systemic inflammation in claudicants' (Eur J Vasc Endovasc Surg., 2004, February, 27(2), pages 201 to 209) report that chronic electrical muscle stimulation is an effective treatment for alleviating intermittent claudication. The technique, by targeted activation of a small muscle mass, does not engender a significant systemic inflammatory response.

A method of neuro-muscular stimulation for the prevention of venous thrombosis and pulmonary embolism is disclosed in U.S. Pat. No. 5,358,513. The method comprises applying electrical stimulation to the subject by means of electrodes attached to an anterior portion of the subject's knee immediately proximal the common peroneal nerve. The electrical stimulation is applied as trains of pulse modulated sinusoids.

CN 1408325 concerns an orthopaedic device for treatment of feet and ankles. The device comprises an ankle and foot bearing plate for providing electrical stimulation to the foot and ankle of a user.

WO 2008/005865 discloses an orthosis and method of its use in the treatment of dropfoot. The orthosis comprises a plurality of sensors for detecting the position of a user's foot and a system for providing electrical stimulation to the appropriate muscles of the user to modify their gait.

A device for providing electrically stimulated massage to a users foot is described in CN 102058200.

U.S. Pat. No. 6,615,080 discloses the neuroelectrical stimulation of the foot muscles of a subject for the prevention of deep vein thrombosis (DVT), pulmonary embolism (PE) and lower extremity edema. The method comprises applying electrical pulses to the muscles of the foot, in particular in a square wave pattern of variable frequency, duration, intensity, ramp time and on-off cycle. The electrical stimulation is applied to the soles of the feet of the subject, to reduce the pooling of blood in the soleal veins.

Devices for the electrical stimulation of a subject are known and are commercially available. In particular, devices for applying electrical stimulation to the feet of subjects, especially to the plantar muscles, are known and commercially available. One example of such a device is the Circulation Booster™ available from High Tech Health Limited, England. The device comprises a pair of pads. In use the user places their feet on the pads. Electrical stimulation of a variable intensity is then provided through the pads to the feet of the subject.

It would be advantageous if an improved method and device for the electrical stimulation of a subject, in particular for the electrical stimulation of the plantar muscles of the subject, could be provided.

It has now been found that an increase in the venous bloodflow of a subject, while reducing the fatigue of the subject, may be achieved by allowing the foot of the subject, when being electrically stimulated, to move. In particular, it has been found that allowing the angle of the joints in the foot and ankle of the subject to change during the electrical stimulation cycle provides a significant improvement in the venous bloodflow.

Accordingly, in a first aspect, the present invention provides an apparatus for the electrical stimulation of a subject, the apparatus comprising:

a contact member having a contact surface for contacting the plantar surface of a foot of the subject; and means for providing an electrical stimulation cycle to the foot of the subject comprising supplying an electrical current to the contact surface for the electrical stimulation of the plantar muscles of the foot of the subject;

wherein the contact surface is moveable so as to allow the angle of the joints of the foot and ankle of the subject to change during the electrical stimulation cycle.

In a further aspect, the present invention provides a method for the electrical stimulation of a subject, the method comprising:

applying an electrical stimulation cycle to the subject comprising providing an electrical current to the plantar surface of the foot of the subject; and allowing the angle of the joints of the foot and ankle of the subject to change during the electrical stimulation cycle.

By way of the present invention, the foot of the subject is allowed to move about the joints of the foot and ankle during the electrical stimulation cycle. In particular, natural movement of the foot is permitted. Movement of the foot may arise in one or more ways. First, depending upon the intensity of the electrical stimulation, in particular the current being applied to the foot of the subject, the muscles of the foot and leg of the subject may be caused to spasm sufficiently to cause the foot to move. In this event, natural movements of the foot about the joints in the leg are allowed. In this way, the electrical stimulation of the foot is not impaired. Further, the subject may move the leg during the stimulation cycle as may be required, for example to change the position of the leg and foot for reasons of comfort. Again, this movement is permitted in the present invention, without adversely affecting the electrical stimulation of the foot.

By allowing the foot of the subject to move during the electrical stimulation cycle, the apparatus and method of the present invention allow the action and effects of voluntary exercise to be more closely replicated. It has been found that allowing or inducing movement of the foot of the subject can increase the venous bloodflow of the subject and significantly alleviate venous stasis. Further, it has been found that fatigue induced as a result of the electrical stimulation is reduced. Still further, permitting movement of the subject's foot can improve the training response of the electrical stimulation treatment.

In the present invention, an electrical stimulation cycle is applied to the foot of the subject. In particular, an electrical current is applied to the plantar surface of the foot, thereby stimulating the plantar muscles of the foot of the subject. The electrical stimulation cycle is applied to the plantar surface of the foot through a contact member having a contact surface. The subject places their foot on the contact member of the apparatus such that the plantar surface of the foot is in contact with the contact surface. The contact surface is electrically conductive, allowing an electrical current to be provided to the plantar muscles of the foot from the apparatus.

The contact surface may have any suitable shape, so as to provide a sufficient contact with the plantar surface of the foot of the subject. Preferably, the contact surface is elongate, having a proximal end, disposed towards the user when in use, and a distal end opposite the proximal end. More preferably the contact surface is of a size and shape to accommodate the major portion of the plantar surface of the foot. It is particularly preferred for the contact surface to be of a sufficient size to accommodate the entire underside of the foot of the subject.

The contact surface may be formed from any suitable material that conducts the electrical current to the plantar surface of the foot of the subject. For example, the contact surface may be formed from a rubber composition comprising carbon, the carbon being present in sufficient amount to provide the requisite electrical conductivity. Alternatively, the contact surface may be formed from metal or from a plastic composition that is electrically conductive or provided with an electrically conductive coating. Other suitable materials for forming the contact member and the contact surface are known in the art.

The contact surface may be flat or substantially flat. Alternatively, the contact surface may be contoured to accommodate the contours of the plantar surface of the foot of the subject. In one embodiment, the contact surface is provided with one or more ridges thereon, the electrical current being provided to the ridges of the contact surface for conducting to the foot of the subject. Alternatively, the contact surface may be smooth or substantially smooth.

Movement of the foot of the subject is permitted throughout the stimulation cycle. Movement of the foot of the subject is provided by having the contact surface moveable, so as to allow the angle of the joints of the foot and ankle of the subject to change during the electrical stimulation cycle, while allowing the user to keep the plantar surface of their foot in contact with the contact surface. The contact surface may be moveable in any suitable way and the contact member may be mounted in any suitable way to allow the contact surface to move under the action of the foot of the subject. In particular, the contact surface is preferably rigid an substantially inflexible, the contact surface being moveable to accommodate the movement of the foot and ankle of the user during use.

In one preferred embodiment, the contact surface is moveable about a pivot. The contact surface may be pivotable about any suitable point of the surface. For example, the contact surface may be pivotable about an end or one side thereof. Preferably, the contact surface is pivotable about a point disposed between two opposing ends or sides thereof. More preferably, the contact surface is pivotable about a mid-point between one or both of the opposing ends or the opposing sides. In particular, the contact surface is pivotable about a point corresponding to the mid-point of the longitudinal arch of the foot of the subject when the foot is properly placed on the contact surface, with the contact surface pivoting about an axis extending laterally across the foot of the subject. In this way, the foot of the subject is able to rock, in particular forwards and backwards from the subject, about the mid-point of the longitudinal arch of the foot during the electrical stimulation cycle, preferably to allow the foot to move naturally about the joints in the foot and the ankle.

In one embodiment, the contact member comprising the contact surface is pivotably mounted to the apparatus.

In an alternative embodiment, the apparatus is provided with a base member for resting on a surface, such as a floor, when in use. The contact member is fixed in relation to the base member. However, the base member is arranged to pivot on the surface. In a preferred embodiment, the base member is provided with a pivot member projecting therefrom, in use the pivot member being in contact with the surface on which the apparatus is resting. The pivot member is positioned such that the base member may move about the pivot member relative to the surface on which the apparatus is standing or resting. The base member may be pivotable about any suitable point thereby to allow the contact surface to pivot, as described above.

In one preferred embodiment, the entire apparatus is pivotable about a pivot member extending from the base thereof. In particular, the apparatus may comprise a housing having the contact surface disposed on an upper portion thereof and a base member forming the base of the housing, the pivot member extending from the base thereof, whereby the housing is pivotable about the pivot member when resting on a surface, such as a floor. In this respect, the term 'upper' is a reference to the orientation of the apparatus when in normal use. The contact surface may be fixed in relation to the housing and moveable therewith.

The pivot member may be any suitable member. For example, the pivot member may comprise a projection extending from the base member or a plurality of projections, for example first and second spaced apart, symmetrically arranged projections, the contact surface being pivotable about the line joining the two spaced apart projections.

The projections may be any suitable shape and size, preferably being rounded to allow for easy pivoting of the contact surface about the projection.

Alternatively, the pivot member may comprise one or more wheels or rollers extending from and rotatably mounted to allow the base member to pivot. Preferably, the apparatus comprises a pair of wheels or rollers mounted so as to rotate about a single axis, the said axis providing the axis about which the contact surface of the apparatus is free to pivot. The wheels or rollers may be mounted to rotate independently or may be mounted to a single axle for rotation together.

The apparatus may comprise a single contact surface for the electrical stimulation of the plantar surface of one foot of the subject. Alternatively, and more preferably, the apparatus may comprise two contact surfaces, allowing the subject to have both feet electrically stimulated at the same time.

The apparatus further comprises means for providing an electrical stimulation cycle to the foot of the subject. The electrical stimulation cycle comprises supplying an electrical current to the contact surface for the electrical stimulation of the plantar muscles of the foot of the subject. The means for providing the electrical stimulation may be any suitable means for generating the electrical current and supplying the current to the contact surface for applying to the plantar surface of the foot of the subject. Suitable means are known in the art.

One system for providing electrical stimulation to the foot of a subject comprises a power supply unit for providing a supply to electricity. The power supply unit may be any suitable supply unit, preferably one connectable to a domestic electrical supply. The system may further comprise a processor for operating control electronics for providing a voltage. This in turn is provided to a transformer to step the voltage up to a level suitable for administering to the foot of the subject. The processor further operates a pulse control circuit, for generating electrical pulses of the required shape and duration. These are provided to the contact surface of the apparatus. The contact surface is provided with a first portion connected to the electrically positive side of the system and a second portion connected to the electrically negative side of the system. The aforesaid portions are arranged such that a subject placing there foot on the contact surface bridges the two portions and completes the electrical circuit, allowing current to flow between the portions through the foot of the subject. In embodiments of the apparatus in which first and second contact surfaces are provided, one for each foot of the subject, the first and second contact surfaces may provide the first and second portions, such that the user places a foot on each contact surface, thereby allowing electrical current to flow through one foot to the other.

The electrical stimulation may be provided to the plantar surface of the foot of the subject in any suitable form. Suitable regimes for the electrical stimulation are known in the art and may be applied in the apparatus and method of the present invention. In particular, the electrical stimulation may be provided by way of a cycle of varying current having a waveform, for example a square or sinusoidal waveform. The current cycle may be continuous or intermittent. The current cycle is preferably variable, allowing the subject to vary such parameters as the frequency of the current, its peak value, and the duration of a stimulation cycle.

In one preferred embodiment, the means for providing electrical stimulation to the foot of the subject is operable to generate a plurality of pulses of electrical current. The operating parameters of the pulses, such as the peak value of the current, the frequency of the pulses, the on/off periods of the pulses, and the waveforms, are preferably variable.

The apparatus is preferably provided with a suitable control panel with controls to allow the subject to vary the aforementioned parameters of the electrical stimulation.

In use, the apparatus is placed on a suitable surface, such as a floor. The subject places a foot on the apparatus, such that the plantar surface of the foot is in contact with the contact surface of the apparatus. The apparatus is activated to provide a cycle of electrical stimulation to the foot of the user in which an electrical current is applied to the plantar surface of the foot through the contact surface. During the stimulation cycle, the foot and leg of the subject may be caused to move involuntarily, due to the stimulation of the muscles of the foot and leg by the electrical current being applied. For example, the muscles of the foot and leg are stimulated into movement by the application of a varying current to the plantar surface of the foot. The current may be applied at a frequency and magnitude to induce sufficient action in the muscles to cause movement of the foot and leg. This movement is accommodated by the apparatus, by the contact surface moving to allow the movement of the foot and leg to occur naturally and with as low impediment as possible. In addition, during the stimulation treatment, the subject may wish to change the position of the foot or leg, for example to increase comfort. Again, such movement is accommodated by movement of the contact surface of the apparatus.

The apparatus may comprise locking means to releasably secure the contact surface from moving. Such locking means provide the facility for the subject to immobilise the contact surface, thereby providing a stable, fixed platform for the foot. This may be preferred in the case of a subject that is infirm or has limited movement in the feet and legs.

Any suitable locking means may be provided to lock the contact surface in place and prevent it from moving, in particular to prevent movement of the contact surface relative to the rest of the apparatus or relative to a surface on which the apparatus is standing. For example, in embodiments in which the contact surface is pivotable about a pivot member, such as a projection, wheel or roller extending to the surface on which the apparatus is resting, the projection, wheel or roller may be retractable to a position in which the apparatus may contact the surface in a stable position, such as by resting on a plurality of spaced apart feet. Alternatively, the apparatus may comprise one or more extendable feet, that may be extended from the base member to provide a stable support for the apparatus.

In one preferred embodiment, the pivot member, such as a projection, wheel or roller, is moveable between a first position and a second position. The first position is one in which the pivot member contacts the surface on which the apparatus is standing below the apparatus and in which position the apparatus can pivot about the pivot member with the foot of the user placed in a normal position on the contact surface. In the first position, the pivot member is most preferably positioned below or substantially below the mid-point of the longitudinal arch of the foot of the user, when the apparatus is in use on a surface and the foot of the user is in the normal position on the contact surface. In the second position, the pivot member extends from the apparatus and contacts the surface on which the apparatus is standing so as to prevent the apparatus from pivoting about the pivot member, when in normal use. In this second position, the pivot member may be outside the normal footprint of the apparatus, but is preferably within the apparatus footprint.

In one preferred embodiment, the pivot member comprises part of a pivot assembly, the pivot assembly being moveably mounted to the apparatus, so as to move between the first and second positions. Preferably, the pivot assembly is pivotably mounted to the apparatus.

Embodiments of the present invention will now be described, by way of example only, having reference to the accompanying drawings, in which.

Figure 1:
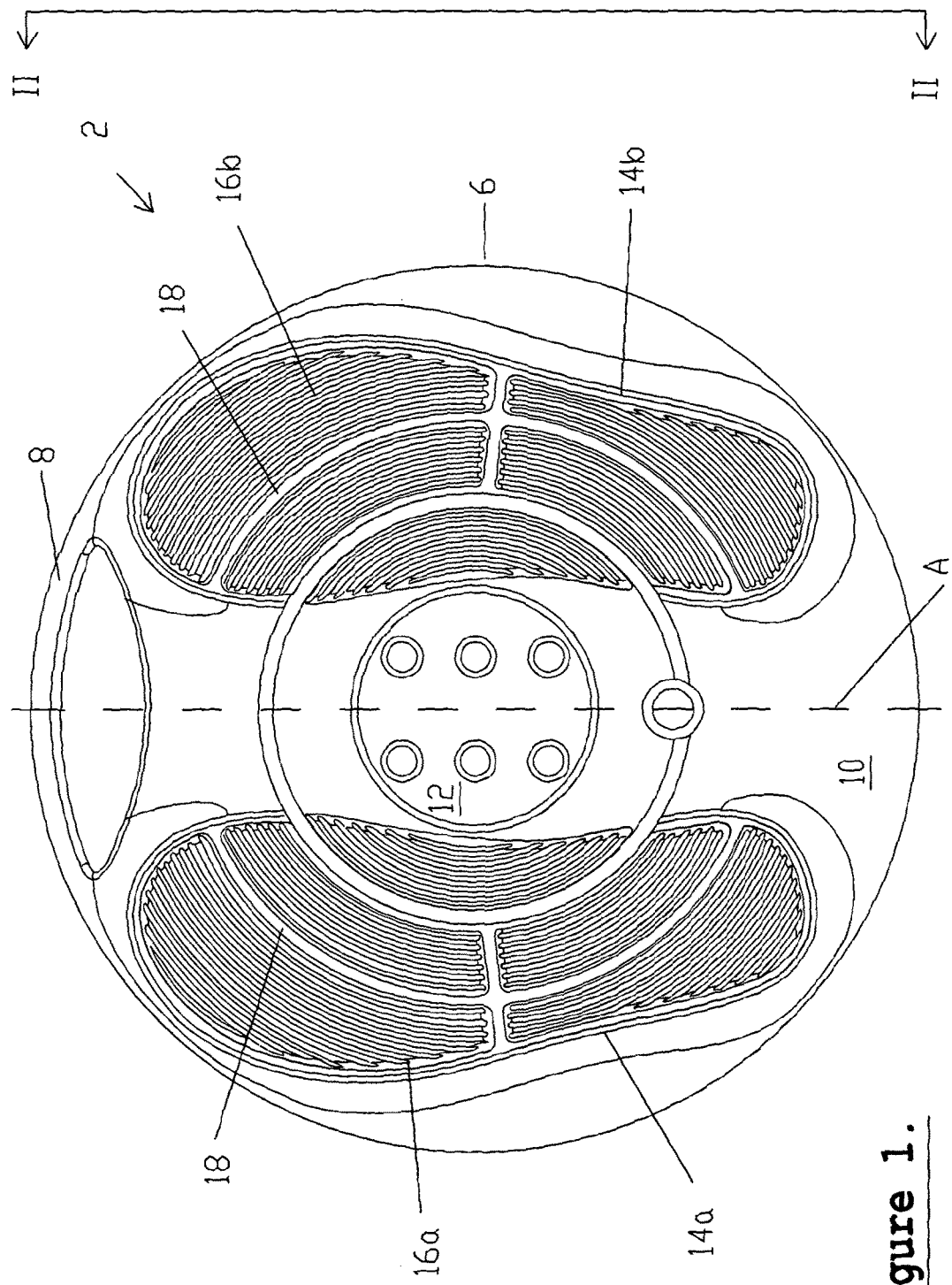
FIG. 1 is a plan view of an apparatus according to one embodiment of the present invention.
Figure 4A:
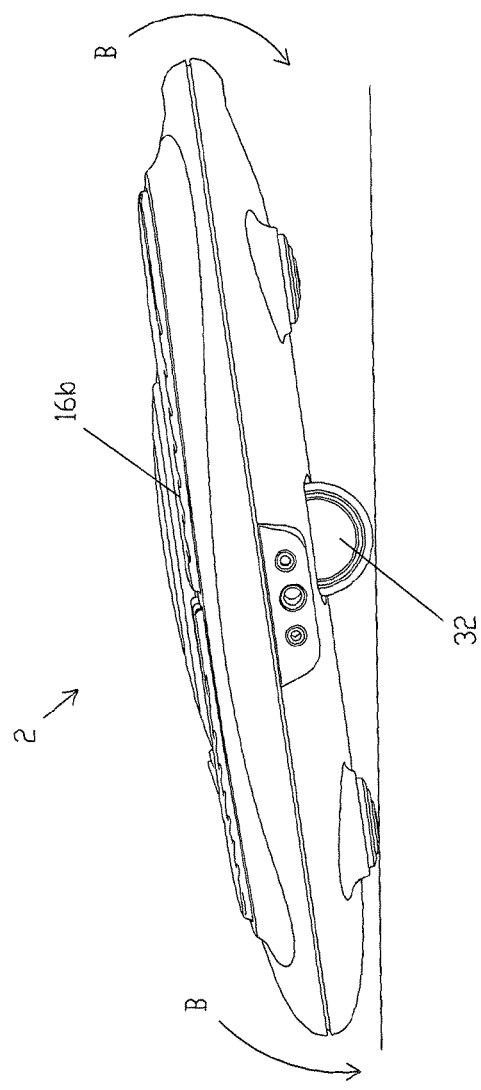
Figure 4B:
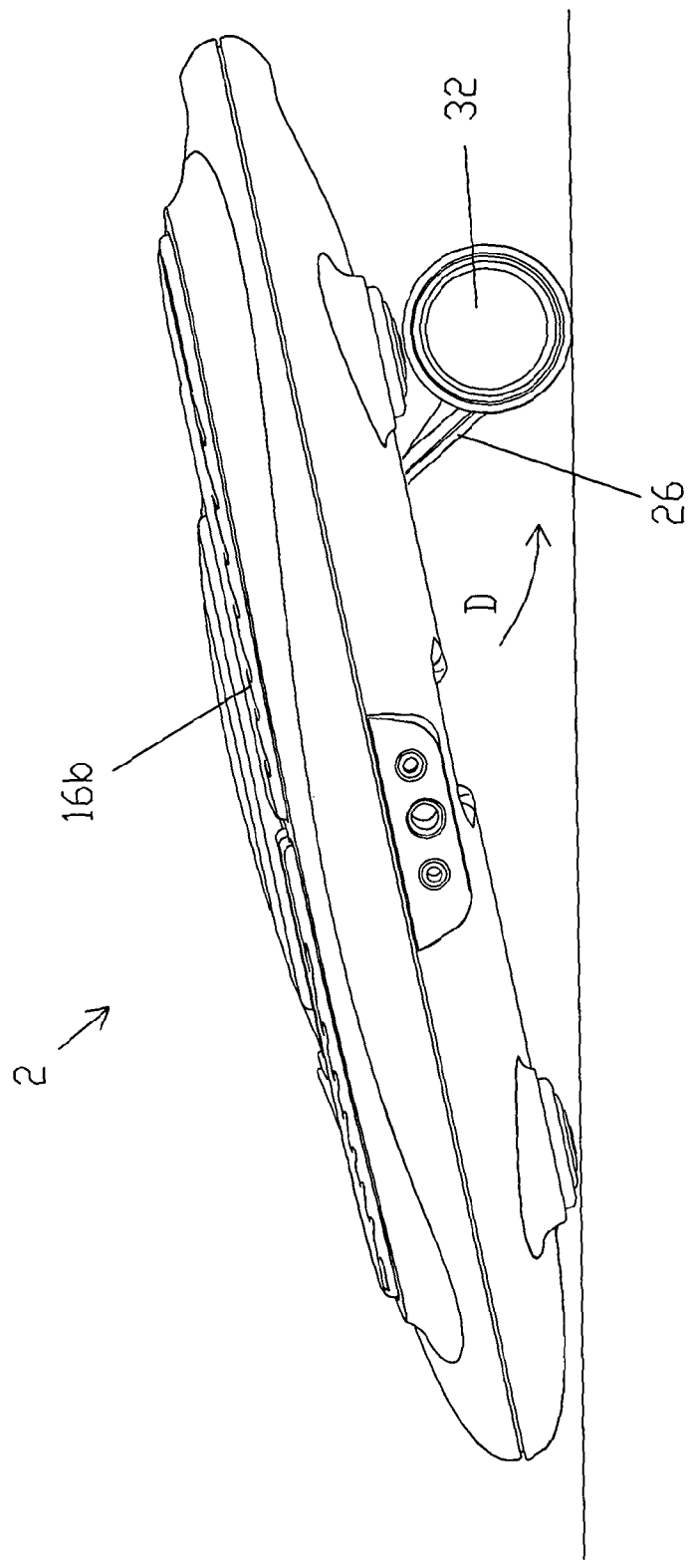
Figure 5:
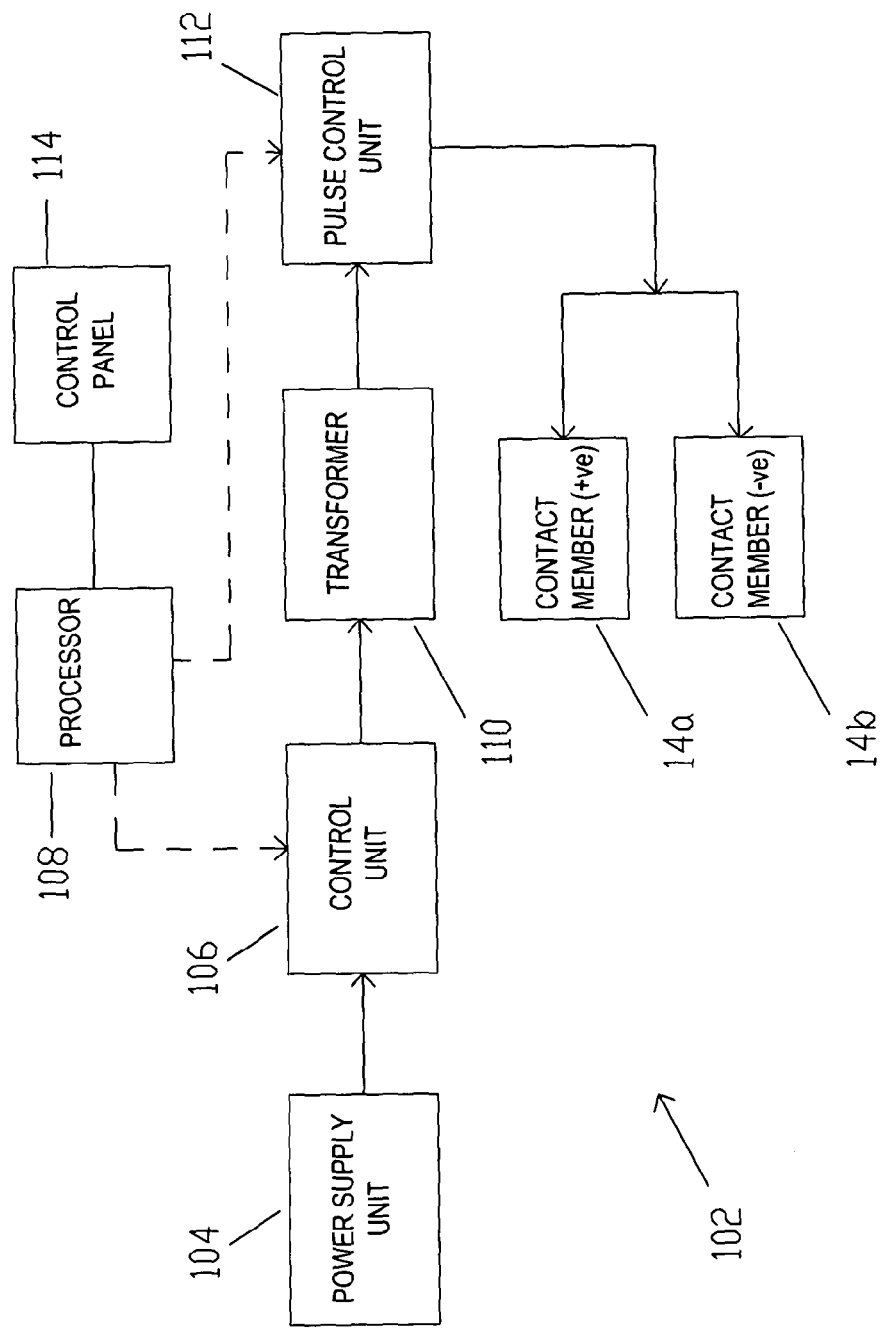

FIG. 4*a* is a side elevation of the apparatus of FIG. 1 in a first operating position;

FIG. 4*b* is a side elevation of the apparatus of FIG. 1 in a second operating position; and FIG. 5 is a schematic diagram of one embodiment of a system for generating electrical pulses for use in the apparatus of the present invention.

Turning to FIG. 1, there is shown, in plan view, an apparatus for the electrical stimulation of the plantar surface of a foot of a subject. The apparatus is generally indicated as 2. The apparatus 2 is shown in side view in FIG. 2 resting on a surface 4, as it would be positioned in normal use by a subject.

Figure 2:
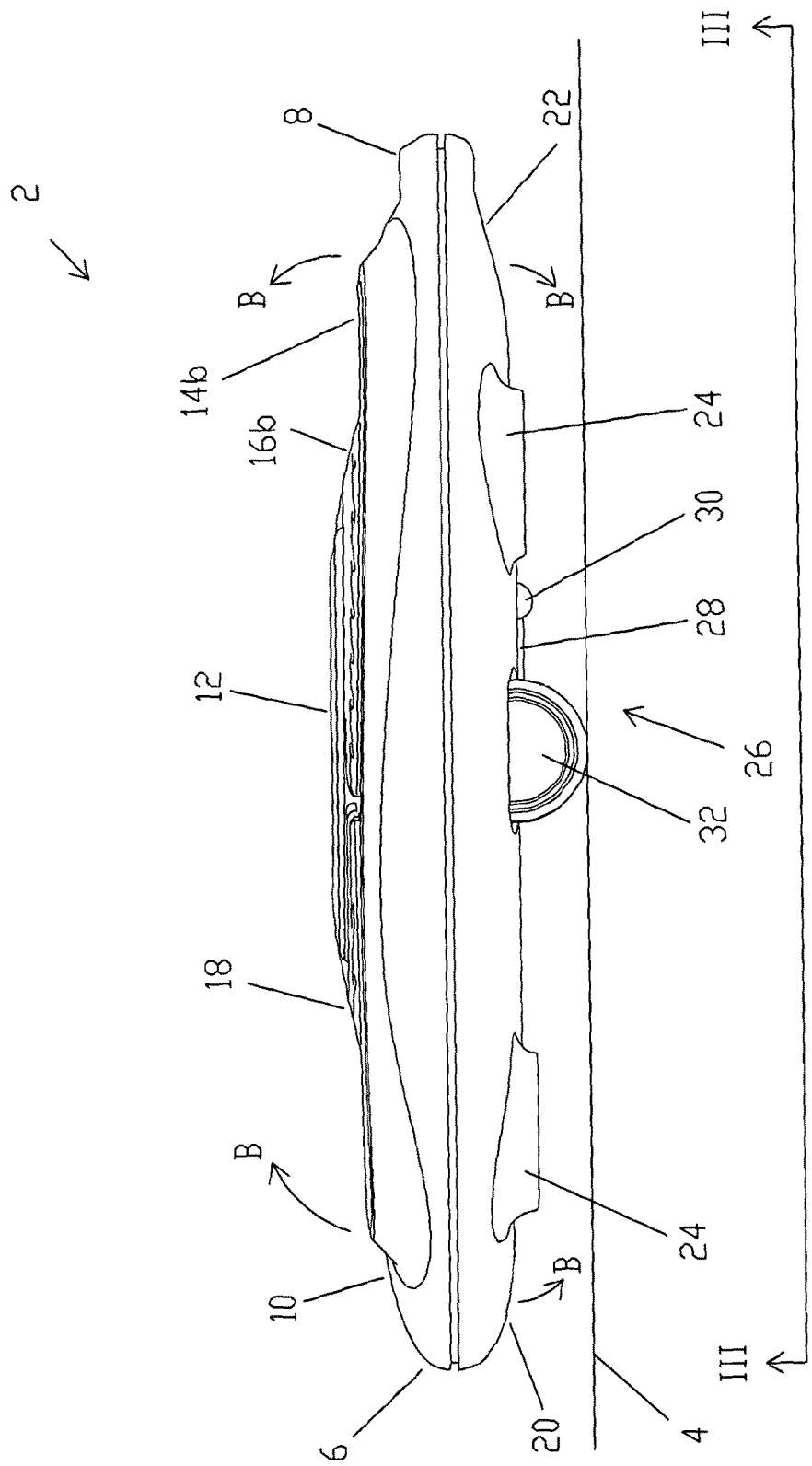
FIG. 2 is a side elevation of the apparatus of FIG. 1 along the line II-II, with the apparatus resting on a surface as in normal use.

The apparatus 2 comprises a generally circular housing 6. The housing 6 is provided at an edge portion with a carrying handle 8. The upper surface 10 of the housing is shown in FIG. 1. In this respect, the terms 'upper' and 'lower' are references to the orientation of the surfaces and components when in the position of normal use as shown in FIG. 2. Thus, the upper surface 10 as shown in FIG. 1 is that surface presented to the subject when the apparatus is set on a surface for use.

The housing 6 contains a means for providing electrical stimulation to the plantar surface of the foot of the subject. The system includes a control panel 12. The control panel 12 is disposed centrally in the upper surface 10 of the housing 6, with controls allowing the subject to activate and adjust parameters of the electrical stimulation cycle to be applied to their foot.

The housing 6 is provided with first and second contact members 14*a*, 14*b* having respective contact surfaces 16*a*, 16*b*. The contact member 14*a*, 14*b* are rigid. The contact members 14*a*, 14*b* are arranged such that the contact surfaces 16*a*, 16*b* are disposed symmetrically on opposing sides of the central control panel 12. Each contact surface 16*a*, 16*b* is generally elongate and is shaped to resemble the general outline of a foot. The contact surfaces 16*a*, 16*b* are of a size to accommodate the entire plantar surface of a foot of the subject. The contact surfaces 16*a*, 16*b* are shaped to correspond to the left and right feet of the subject, respectively, as shown in FIG. 1.

Each contact surface 16*a*, 16*b* is provided with a plurality of arcuate ridges 18 thereon. Alternatively, the contact surfaces 16*a*, 16*b* may be smooth or substantially smooth.

In use, the means for providing electrical stimulation to the feet of the subject provides an electric current to the contact surfaces 16*a*, 16*b* for conducting to the plantar surface of the corresponding foot of the subject.

Figure 3:
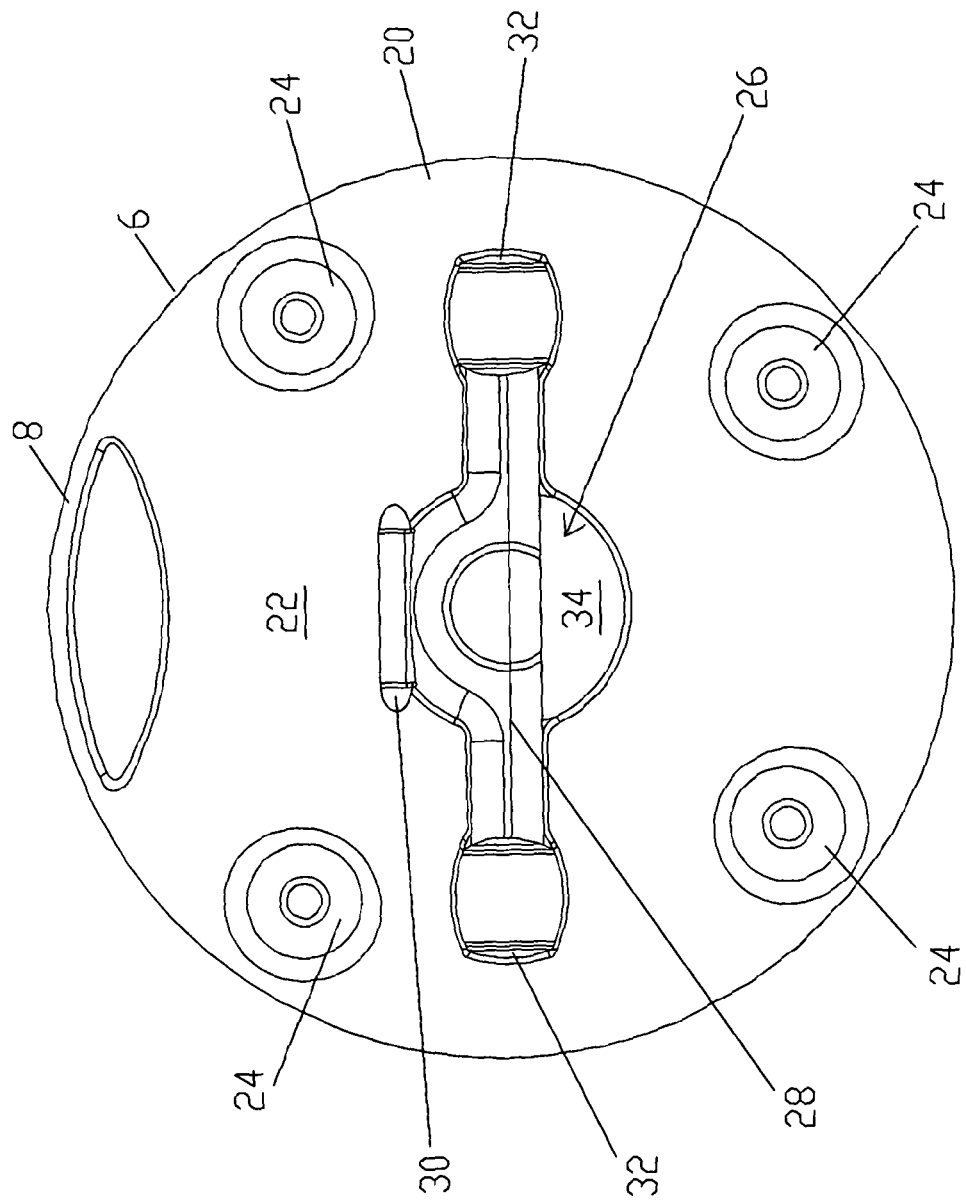
FIG. 3 is a view of the base of the apparatus along the line III-III of FIG. 2.

The apparatus 2 can be considered to have a central axis A, shown in FIGS. 1 and 3. In normal use, this central axis A extends away from the subject, with the subject placing their feet on either side of the central axis A.

Turning to FIGS. 2 and 3, the housing 6 has a base 20 providing the housing with a lower surface 22. As shown in FIG. 2, the lower surface 22 faces the surface on which the apparatus is set, when in normal use. The housing 6 is provided with four generally circular feet 24 extending from the base 20 and the lower surface 22. The feet 24 are arranged in a symmetrical pattern about the central axis A.

The base 20 is further provided with a rocker assembly, generally indicated as 26. The rocker assembly 26 comprises an axle assembly 28 pivotably mounted to the base 20 by a mount 30. An axle (not visible in the figures) extends within the axle assembly 28 across the base 20 substantially perpendicular to the central axis A. A wheel 32 is mounted to the axle at each end of the axle assembly 28. The wheels 32 may be mounted to the axle assembly, so as to rotate. More preferably, the wheels 32 are fixed and not rotatable relative to the axle assembly.

The base 20 is provided with a recess 34 in the lower surface 22, with the rocker assembly 26 being accommodated within the recess 34 and extendable from the recess by movement about the mount 30.

The rocker assembly 26 is arranged such that, with the wheels 32 positioned as shown in the figures, the housing 6, together with the contact surfaces 16*a*, 16*b*, pivots about the wheels 32, as indicated by the arrows B in FIG. 2. The axle assembly 28 is arranged to position the axis of rotation extending between the wheels 32 to be at the mid-point between the proximal and distal ends of the contact surfaces 16*a*, 16*b*. With the feet of the subject properly positioned on the contact surfaces 16*a*, 16*b*, this places the axis of movement of the contact surfaces at the centre of the longitudinal arch of each foot. This in turn allows the apparatus 2, and hence the contact surfaces 16*a*, 16*b*, to rock forwards and backwards and permit the natural movement of the feet and ankles of the subject.

In use, the apparatus has two operating positions, as shown in FIGS. 4*a* and 4*b*. In normal use, the rocker assembly 26 is positioned within the recess, as shown in FIG. 2 and described in detail above. The apparatus 2 is placed on a surface 4, as shown in FIG. 4*a*. The subject places their feet on the respective contact member 14*a*, 14*b*, with the plantar surfaces firmly in contact with the contact surfaces 16*a*, 16*b*. Electrical stimulation of the feet is activated using the control panel and a cycle of electrical current is applied to the plantar surfaces of the subject's feet through the contact surfaces. Depending upon the parameters of the current cycle, involuntary movement of the feet and legs may be induced by the electrical stimulation. Alternatively, or in addition, the subject may move their feet and legs voluntarily during the stimulation cycle. Such movement is accommodated by the housing 6 rocking about the axis of the wheels 32 as indicated by arrows B in FIG. 2 and FIG. 4*a*. In particular, the forwards and backwards rocking motion allows the natural movement of the joints in the feet and ankles of the subject to take place unimpeded.

The user may not require the rocking action of the apparatus during the stimulation cycle, for example as a result of infirmity or disability, the rocking action may be prevented as shown in FIG. 4*b*. In particular, the axle assembly 26 is pivoted about the mount on the base, as indicated by arrow D in FIG. 4*b*. This moves the wheels 32 away from below the mid-point of the contact surfaces 16*a*, 16*b* and forwards from the user, that is to the left as viewed in FIG. 4*b*. In addition, the apparatus 2 is raised at an angle to present the contact surfaces 16*a*, 16*b* to the user, as shown in FIG. 4*b*. With the axle assembly 26 in the extended position shown in FIG. 4*b*, and with the feet of the user in the normal position on the contact surfaces 16a, 16b, the apparatus is held in a stable position on the surface and does not rock. Electrical stimulation of the feet of the user proceeds as described above and is unchanged.

The rocking action may be restored simply by moving the axle assembly 26 into the retracted position, shown in FIG. 4a.

Referring to FIG. 5, there is a shown a schematic diagram of one embodiment of a system for generating electrical pulses for the stimulation of the feet of a subject. The system, generally indicated as 102, is suitable for use in the apparatus of FIGS. 1 to 4.

The system 102 comprises a power supply unit 104, for example connectable to an electrical power supply, such as a domestic electrical supply. The power supply unit 104 outputs an electrical current, the voltage of which is adjusted, as required by a control unit 106, under the action of a processor 108. The adjusted voltage is stepped up by a transformer 110, before being fed to a pulse control unit 112, also operated by the processor 108. The pulse control unit generates a pulsed electrical signal having the desired pulse shape and duration, under the action of the processor. The output of the pulse control unit 112 is connected to the first and second contact members 14a, 14b of the apparatus of FIG. 1. A control panel 114 provides a user interface for controlling the processor 108.

In use, by placing their feet on the contact surfaces of the contact members 14a, 14b, the user completes an electrical circuit, allowing the pulsed electrical signal to travel from one foot to the other and stimulate muscle contraction in the feet and legs of the user. As described above, the rocking action of the apparatus allows the feet and legs of the user to move, in particular about the joints in the feet and ankles, as required under the action of the electrical stimulation of the muscles.

The invention claimed is:

1. An apparatus for the electrical stimulation of a subject, the apparatus comprising:
   a first contact member having a first contact surface for contacting the plantar surface of a first foot of the subject and a second contact member having a second contact surface for contacting the plantar surface of a second foot of the subject; and
   means for providing an electrical stimulation cycle to the foot of the subject comprising supplying an electrical current to the first and second contact surface for the electrical stimulation of the plantar muscles of the foot of the subject when the subject places the first foot on the first contact surface and the second foot on the second contact surface, wherein the first contact surface is of opposite polarity to the second contact surface and the electrical current flows through the first foot to the second foot of the subject;
   wherein the first and second contact surfaces are moveable so as to allow the angle of the joints of the feet and ankles of the subject to change during the electrical stimulation cycle; and
   wherein the apparatus further comprises a pivot member, each of the first and second contact surfaces being integral with the pivot member and pivotable about the pivot member at a position between opposing ends or opposing sides of the first and second contact surfaces.

2. The apparatus according to claim 1, wherein each of the first and second contact surfaces are elongate, having a proximal end and a distal end.

3. The apparatus according to claim 2, wherein each of the first and second contact surfaces can accommodate the major portion of the plantar surface of a respective one of the first and second feet of the subject.

4. The apparatus according to claim 3, wherein each of the first and second contact surfaces are contoured to accommodate the contours of a respective one of the first and second feet of the subject.

5. The apparatus according to claim 1, further comprising locking means operable to releasbly lock the first and second contact surfaces to prevent movement thereof during use.

6. The apparatus according to claim 5, wherein the pivot member is moveable between a first position, in which each of the first and second contact surfaces are moveable and a second position in which movement of each of the first and second contact surfaces are prevented.

7. The apparatus according to claim 6, wherein the pivot member is a projection extending from a base member of the apparatus, the pivot member being moveable between a first position, in which the apparatus is pivotable about the pivot member relative to a surface on which the apparatus is standing, and a second position in which the apparatus is not pivotable about the pivot member.

8. The apparatus according to claim 7, wherein in the first position the pivot member is configured to lie below the mid point of the longitudinal arch of each of the first and second feet of the user.

9. The apparatus according to claim 8, wherein in the second position, the pivot member lies in front of the mid point of the longitudinal arch of each of the first and second feet of the user.

10. The apparatus according to claim 7, wherein the apparatus comprises a pivot assembly moveably mounted to the apparatus so as to be moveable between the first and second positions, the pivot assembly comprising the pivot member.

\* \* \* \* \*